United States Patent [19]

Mischke

[11] Patent Number: 5,110,206
[45] Date of Patent: May 5, 1992

[54] DEVICE FOR FORMING A COMPOSITE IMAGE OF A PERSON'S FACE

[76] Inventor: Todd E. Mischke, 95-1195 Leolani St., Mililani, Hi. 96789

[21] Appl. No.: 694,486

[22] Filed: May 2, 1991

[51] Int. Cl.$^5$ ............................................. G03B 21/14
[52] U.S. Cl. ........................................ 353/30; 353/35; 353/DIG. 3; 434/404
[58] Field of Search ............ 353/30, 32, 35, 25, 353/41, 40, 121, DIG. 3; 434/370, 368, 404, 402

[56] References Cited

U.S. PATENT DOCUMENTS

| | | | |
|---|---|---|---|
| 2,488,955 | 11/1949 | Wood. | |
| 2,520,347 | 8/1950 | Talcott | 434/404 |
| 2,813,457 | 11/1957 | Fitzgerald | 353/35 |
| 2,887,006 | 5/1959 | Yale | 353/35 |
| 3,122,859 | 3/1964 | La Reaux, Jr. | |
| 3,195,400 | 7/1965 | Dlott | 353/30 |
| 3,209,643 | 10/1965 | Jouker | 353/35 |
| 3,277,777 | 10/1966 | Hendrick | 353/35 |
| 3,336,681 | 8/1967 | Minasy. | |
| 3,620,611 | 11/1971 | Parrent, Jr. | 353/30 |
| 3,687,536 | 8/1972 | Gorrell | 353/35 |
| 3,975,094 | 8/1976 | Boggs | 353/35 |
| 4,050,809 | 9/1977 | Boggs | 353/35 |
| 4,756,614 | 7/1988 | Kato et al. | 353/35 |

FOREIGN PATENT DOCUMENTS 7628223  5/1978  France ................... 353/35

Primary Examiner—William A. Cuchlinski, Jr.
Assistant Examiner—William C. Dowling
Attorney, Agent, or Firm—Eugene M. Eckelman

[57] ABSTRACT

A transparent viewing sheet has a plurality of facial features outlined thereon and is used for form am image by viewing the facial features thereon. Rotatably concentric transparent facial feature rings are disposed in overlaid relation with each other and have different facial features outlined thereon but in different shapes and sizes. The facial feature rings are rotatably movable relative to each other and are arranged to align a plurality of facial features at a common point in their overlaid position to form an image as is it appeared in the viewing sheet. The facial feature rings are mounted on a base sheet having a viewing window therein whereby to view the formed image. The transparent viewing sheet may be used in combination with a mirror to form an image to be used to form the completed image. In the method of the invention, a person's image is determined through a transparent viewing sheet having a plurality of different facial features outlined thereon and matching these facial features with facial features on respective overlaid transparent rotatable rings connected in concentric relation. The rings are rotatably positioned relative to a viewing window such that the method facial features on the rings are all aligned whereby to form a composite image.

11 Claims, 2 Drawing Sheets

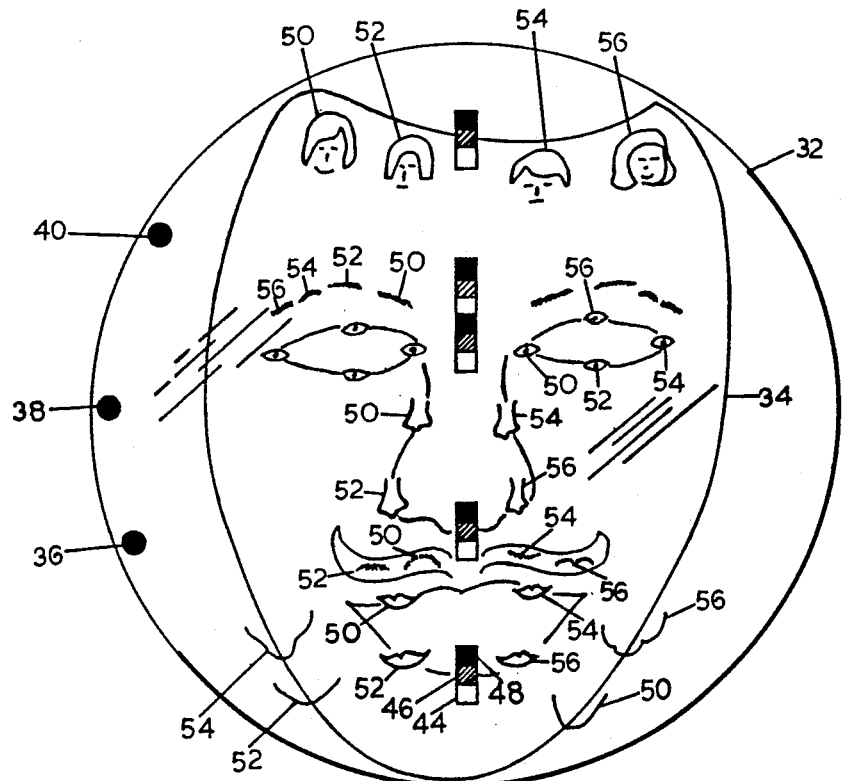
FIG. 3
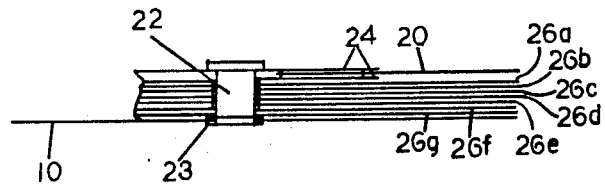
FIG. 4
| put check marks under the selected colors. | outer color | | | middle color | | | inner color | | | |
|---|---|---|---|---|---|---|---|---|---|---|
| | size | | | location | | | shape | | | |
| | Red | Blue | Green | Red | Purple | Black | Red | Green | Blue | Purple |
| | smaller larger same as color outline | | | color level of each feature from chin | | | choose one of the four different shapes | | | |
| head hair | | | ✓ | ✓ | | | | | | ✓ |
| brows | ✓ | | | | ✓ | | | | ✓ | |
| eyes | ✓ | | | | ✓ | | | ✓ | | |
| nose | | ✓ | | | ✓ | | | | | ✓ |
| lips | ✓ | | | | ✓ | | ✓ | | | |
| chin | | ✓ | | | ✓ | | ✓ | | | |
| facial hair | | ✓ | | | ✓ | | | | ✓ | |
FIG. 5

DEVICE FOR FORMING A COMPOSITE IMAGE OF A PERSON'S FACE

BACKGROUND OF THE INVENTION

This invention relates to new and useful improvements for forming a composite image of a person's face.

Devices have heretofore been patented for creating various pictures or images from composite parts. For example, U.S. Pat. No. 2,488,955 is directed to a device for forming composite images in the form of devices and structures, whereby persons can become aware of the appearance of a room or building before it is completed. U.S. Pat. No. 3,122,859 is directed to a toy device comprising a cylindrical housing utilizing a plurality of telescopically assembled tubes that are independently rotatable relative to one another and with each having a different character thereon so that a person, such as a child, can compose different types of figure pictures. U.S. Pat. No. 3,336,681 utilizes a projector in combination with an assortment of slides that have facial features thereon capable of selective projection so as to provide a pictorial image reconstruction of a person's face.

SUMMARY OF THE INVENTION

According to the present invention and forming a primary objective thereof, a device is provided that has improved structure capable of forming a composite image of a person's face.

A more particular object of the invention is to provide a device of the type described that is compact in structure to the extent that it may be used as a greeting card or at least a flat packaged product capable of being readily sent through the mails.

Another object is to provide a new method of forming a composite image of a person's face.

In carrying out the objects of the invention, a transparent viewing sheet is provided having facial features outlined thereon which are used to compare facial features by viewing images thereof in a mirror and transferring such images to a plurality of independently rotatable concentric transparent facial feature rings connected in overlaid relation with each otter and each having facial features outlined thereon in different shapes and sizes. Means are provided to rotatably position the rings relative to each other to align a plurality of selected facial features at a common viewing point in the overlaid position of the rings, whereby the selected facial features combine to form a completed image. A viewing window is provided in a supporting base sheet for the transparent facial feature rings and can be associated with a printed faceless human body on the rear of the base sheet that combines with the face to form a full body picture. A transparent stationary code ring is disposed in concentric overlaid relation with the facial feature rings and includes a plurality of color codes one for each of the facial features on the facial feature rings. Each of the facial feature rings has a reference point used for aligning it with the code ring to center the chosen facial features in the viewing window.

The invention will be better understood and additional objects and advantages will become apparent from the following description taken in connection with the accompanying drawings.

DETAILED DESCRIPTION OF THE DRAWINGS

FIG. 3 is a plan view of a transparent viewing sheet which has the plurality of facial features outlined thereon.

FIG. 4 is an enlarged fragmentary sectional view taken on the line 4—4 of FIG. 1; and FIG. 5 is a grid sheet that can be used to record the coding of established facial features.

DETAILED DESCRIPTION OF A PREFERRED EMBODIMENT

Figure 1:
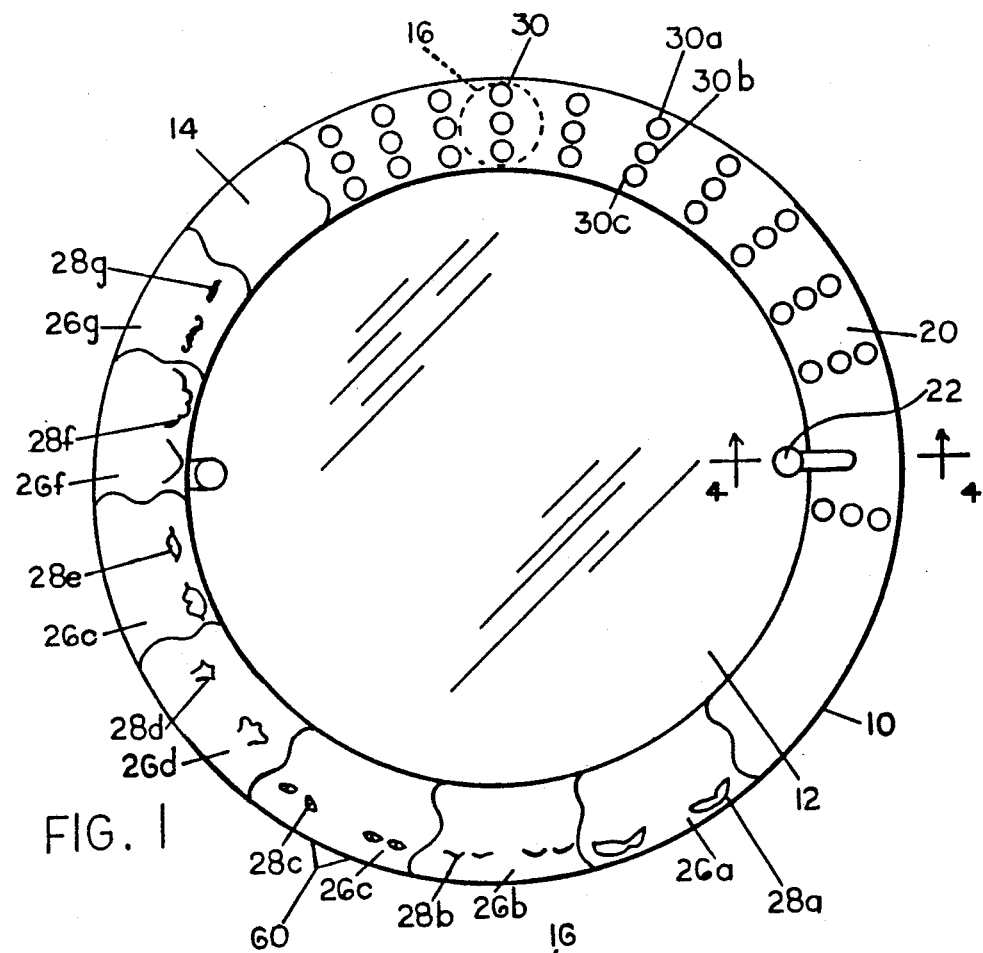
FIG. 1 is a plan view of the present device for forming a composite image of a person's face, portions of the code ring and facial feature rings being broken away to show details of structure.
Figure 2:
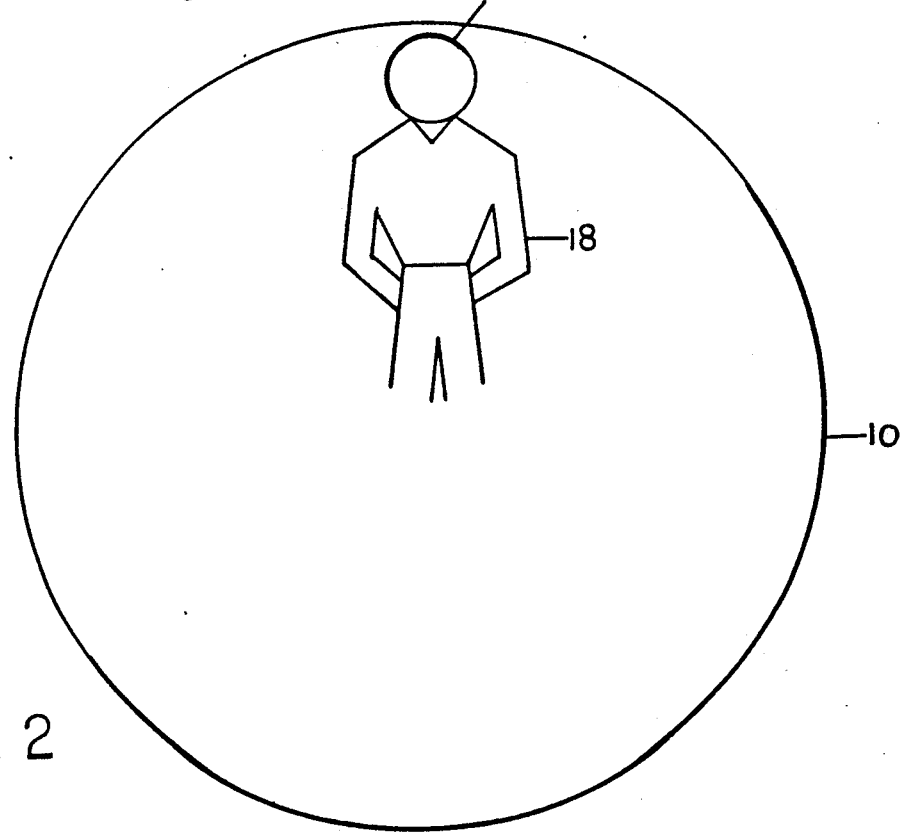
FIG. 2 is a plan view of the rear side of the device.

In its structure, the present device comprises a circular base sheet 10, FIGS. 1 and 2, having an inner mirror portion 12. The mirror portion has a diameter slightly less than the outer diameter of the base sheet forming an outer band portion 14 on the base sheet. The base sheet may comprise cardboard or other thin semi-rigid material, and the mirror preferably comprises a reflective aluminum type coating on the base sheet. Such a structure can comprise a minimum over-all thickness and one which is capable of being formed into a greeting card and easily mailable. Also, it does not possess any hazardous or breakable parts. The outer band portion 14 is provided with a window 16 that is viewed from the rear side of the base sheet, as will be described in more detail hereinafter, and that is arranged to contain a composite image when the process of the invention is finished. A faceless person 18, FIG. 2, is printed on the rear side of the base sheet in combination with the viewing window.

A code ring 20 is secured to the base sheet 10 by a pair of spacer connectors 22, best seen in FIG. 4. These connectors have a clamp portion 23 for integral securement to the base sheet 10 and have outwardly extending clamp portions 24 at the top that in turn are secured integrally to the code ring 20. Thus, the code ring 20 is mounted in a stationary position on the base sheet.

Confined rotatably between the radially extending clamp portions 24 and the base sheet are rings 26a, 26b, 26c, 26d, 26e, 26f and 26g having facial features printed thereon comprising hairstyles 28a, brows 28b, eyes 28c, noses 28d, lips 28e, chins 28f and facial hair 28g, respectively. The rings 26a through 26g are transparent except for the facial feature that is printed thereon, and these rings, being confined between the code ring 20 and the base sheet 10 are rotatable relative to the code ring and also relative to each other.

Code ring 20 has a plurality of radial rows 30 of three dots 30a, 30b and 30c each located selectively around the ring in equally spaced relation. The number of rows 30 of the dots is equal to and similarly spaced relative to the facial features 28a through 28g whereby as will be apparent, combinations of colors in the rows can be matched with colored image symbols on a transparent viewing sheet 32, FIG. 3, to be described. For purposes of illustration, the rows 30 of colored dots are spaced 10 degrees apart, and with this spacing and different combinations of colors, 36 different rows of facial feature combinations are available. The outer row 30a of dots designates size, the center row 30b designates distance from the bottom of the chin, and the inner row 30c designates shape.

The combination of coded dots 30 to be used is determined by the transparent viewing sheet 32 having the outline of a face 34 thereon. This face outline is preferably approximately life size and is minus the hairline. Within or on the outline 34 are the color coded symbols mentioned above that can be matched in color with dots on the code ring. Three color symbols 36, 38 and 40, such as red, blue and green, respectively, appear at the outer edge of the transparent viewing sheet 32 and designate smaller, larger, and same size. A set of three central, colored symbols 44, 46, and 48, such as red, purple and black, respectively, is provided to designate the vertical relation of each of the mouth, nose, eyes, brows and head hair, as compared with the bottom of the chin of outline 34. In addition four color symbols 50, 52, 54, and 56 such as red, green, blue and purple, respectively, appear at selected places directly on the outline 34 to designate four different shapes.

Each of the facial feature rings 26a through 26g has a tab 60 which is visible to the operator and which can be used to rotate the rings 26 relative to the code ring 20 according to the information supplied from the transparent viewing sheet 32. As stated, the number of possible color combinations on the code ring 20 is equal to the number of facial features that are printed on the rings 26a through 26g. This ensures that for every possible color combination there is a way to arrange the facial feature rings 26a through 26g to fit the color code description.

OPERATION

A particular use of the invention is for a person to form his or her own face and the following operation of the device will be such a process. It is to be understood, however, that the device can be used for other purposes such as to view and form other persons' faces.

A first step in using the present device to form a person's own face is to hold the transparency viewing sheet 32 between such person and a mirror, such as the mirror 12 on the base sheet 10. Spacing of the transparency viewing sheet 32 from the mirror is adjusted such that the bottom of the person's chin is aligned vertically with the bottom of the chin outlined on the sheet 32. Such mirror viewing can be accomplished in a wall mirror if desired for convenience. Thereupon, the person compares the image from the mirror with color symbols on the outline 34 to establish the size, location and shape of facial features. After finding the appropriate combination of size, location and shape of each facial feature by colors on the sheet 32, the facial feature rings 26a through 26g are rotated with their tabs in alignment with the color coded combination on the code ring 20.

In a more specific illustration in the use of the invention, a person to form a composite image of his or her face holds the transparency viewing sheet 32 between his or her face and views the outline 34 thereof in a mirror. At the same time the person adjusts the spacing of the sheet 32 between the mirror and his or her face whereby to cause the outline 34 to be roughly the same general size as the face. After first aligning the bottom of the outline 34 with the bottom of the person's own chin, the size of each feature, for example the brows, is determined by comparing them with the size of the mirror image. For purposes of illustration herein, it will be considered that the brows size of the mirror image is about the same size as that on the outline 34. A particular color on the edge of the transparency viewing sheet designates "same size" and thus the "same size" color will be noted. As noted above, the same size code color 40 is green. The outer ring 30a of colors on the code ring 30 designates the size. Similarly, the location of the brows from the chin is noted and the color of one of the location symbols 44, 46 and 48 is noted. As an example, it will be considered that the person's brows are lower than the brows on the outline 34. Such location is designated by the color red. Also, while viewing the transparency viewing sheet 32 in the mirror image, the shape of the facial feature is matched with a colored symbol 50, 52, 54, and 56 on the viewing sheet 32 and such colored symbol is noted, for example, purple. The inner ring 30c designates the "shape". Thus, three colors have now been noted, namely, colors designating size, location from the chin, and shape. The tab 60 for the particular facial feature ring, comprising ring 26b, is used to rotate this ring around to find the three color combination on the stationary code ring 30, namely, where green is on the outer ring 30a, red is on the middle ring 30b, and purple is on the inner ring 30c. This places the matching facial features of this one facial feature over the viewing window 16 as viewed from the rear side.

This same procedure is carried out for each facial feature whereupon when all the rings are rotated to their matching colors of the code ring, the viewer will have built a look alike picture of himself or herself.

A printed grid box 62, FIG. 5, may be provided to record the color coding of each of the selected facial feature. That is, the printed color designations in the box comprise the color of symbols on the transparency viewing sheet 34 for each of the three categories on the sheet 34, namely, size, vertical location, and shape. Reading across in the grid box, check marks can be made to record the color combinations to be found in the row 30 so that the rings 26a-26g can be turned to align the tab 60 with proper color coding. When each of the three features has been aligned with its proper coding, the intended face will appear from the rear in viewing window 16 with all the facial symbols combined.

The device is thus compact in its construction and with the many combinations of facial features, a fairly accurate representation can be made. The device is substantially flat in construction and can be utilized as a mailing piece.

It is to be understood that the form of my invention herein shown and described is to be taken as a preferred example of the same and that various changes in the shape, size and arrangement of parts may be resorted to without departing from the spirit of my invention, or the scope of the subjoined claims.

Having thus described my invention, I claim:

1. A device for forming a composite image of a person's own face, comprising:
 a transparent viewing sheet having a plurality of facial features outlined thereon used to form an image by viewing the facial features in a mirror through said viewing sheet,
 a plurality of rotatably concentric transparent facial feature rings in overlaid relation with each other and each having a different facial feature outlined thereon but in different sizes, locations, and shapes,
 and means to rotatably position said rings relative to each other to align a plurality of facial features taken from the mirror at a common point in their overlaid position, whereby the selected facial features combine to form the image as it appeared in said viewing sheet.

2. The device of claim 1 including a base sheet supporting said transparent rings in overlaid concentric rotatable relation, and a viewing window in said base sheet through which said formed image is viewed.

3. The device of claim 2 wherein said base sheet has a rear surface, and a faceless human body printed on said rear surface in association with said viewing window to unit with the face formed by said image.

4. The device of claim 2 wherein said base sheet has a mirrored front surface capable of being used as the mirror to view the facial features through said transparent viewing sheet.

5. The device of claim including a transparent stationary code ring disposed in concentric overlaid relation on said facial feature rings, said code ring including a plurality of code means thereon one for each of said facial features on said facial feature rings.

6. The device of claim 1 including a transparent stationary code ring disposed in concentric overlaid relation on said facial feature rings, said code ring including at least three code means thereon one for each of said facial features on said facial feature rings.

7. The device of claim 6 wherein one of said code means designates the size of the facial feature, a second designates the location of facial features as measured up from the chin, and a third designates the shape of facial features.

8. The device of claim 6 wherein one of said code means designates at least one of three sizes of facial features, a second designates at least one of three locations of facial features as measured up from the chin, and a third designates at least one of four shapes of facial contours.

9. A device for forming a composite image of a person's face comprising:
a transparent viewing sheet having a plurality of facial features outlined thereon used to form an image by comparing the facial features through said viewing sheet,
a plurality of rotatably concentric transparent facial feature rings in overlaid relation with each other and each having a different facial feature outlined thereon but in different sizes, locations, and shapes,
and means to rotatably position said rings relative to each other to align a plurality of facial features taken from comparison at a common point in their overlaid position, whereby the selected facial features combine to form the image as it appeared in said viewing sheet.

10. The method of forming a composite image comprising:
viewing a person's image through a transparent viewing sheet having a plurality of different facial features outlined thereon,
matching each of the person's facial features of the image with facial features on respective overlaid transparent rotatable rings connected in concentric relation,
and rotatably positioning all of said rings relative to a viewing window such that the matched facial features on the rings are all aligned whereby to form said composite image.

11. The method of claim 10 wherein said person's image through said transparent viewing sheet is made by viewing said image in a mirror.

* * * * *